(12) United States Patent
Musa

(10) Patent No.: US 7,319,132 B2
(45) Date of Patent: Jan. 15, 2008

(54) POLYMER COMPOUNDS CONTAINING OXETANE AND MALEIMIDE FUNCTIONALITY

(75) Inventor: Osama M. Musa, Hillsborough, NJ (US)

(73) Assignee: National Starch and Chemical Investment Holding Corporation, New Castle, DE (US)

( * ) Notice: Subject to any disclaimer, the term of this patent is extended or adjusted under 35 U.S.C. 154(b) by 399 days.

(21) Appl. No.: 11/121,430

(22) Filed: May 4, 2005

(65) Prior Publication Data
US 2005/0209437 A1    Sep. 22, 2005

Related U.S. Application Data

(62) Division of application No. 10/430,085, filed on May 6, 2003, now Pat. No. 6,982,338.

(51) Int. Cl.
C08G 18/00 (2006.01)
C07D 405/02 (2006.01)
(52) U.S. Cl. .................................. 528/392; 548/517
(58) Field of Classification Search ................ 528/392; 548/517
See application file for complete search history.

(56) References Cited

U.S. PATENT DOCUMENTS

| 3,867,353 | A | 2/1975 | Hsieh et al. | |
| 6,753,434 | B1 * | 6/2004 | Musa | 549/510 |

OTHER PUBLICATIONS

Ledwith, Anthony: "Possibilities for promoting cationic polymerization by common sources of free radicals"; *Polymer 1978*, vol. 19; October; pp. 1217-1222.
Sasaki, Hiroshi et al.: "Photoinitiated Cationic Polymerization of Oxetane Formulated with Oxirane"; *Journal of Polymer Science Part A*; vol. 33; 1995; pp. 1807-1816.
Searles, Scott et al.: "Hydrogen Bonding Ability and Structure of Ethylene Oxides"; *This Journal*;73;3704;1951.
Xianming, Hu et al.: "Phase-Transfer Synthesis of Optically Pure Oxetanes Obtained from 1,2,2-Trisubstituted 1,3-Propanediols"; *Synthesis May 1995*; pp. 533-538.
Fujiwara, Tomoko et al.: "Synthesis and Characterization of Novel Oxetane Macromonomers"; *Polymer Preprints 2003*; 44(1), 785.
Dhavalikar, R. et al.: "Molecular and Structural Analysis of a Triepoxide-Modified Poly(ethylene terephthalate) from Rheological Data"; *Journal of Polymer Science*: Part A: Polymer Chemistry; vol. 41, 958-969 (2003); pp. 958-969.
Satoh, Toshifumi et al.: "A Novel Ladder Polymer. Two-Step Polymerization of Oxetanyl Oxirane Leading to a "Fused 15-Crown-4 Polymer" Having a High Li+-Binding Ability"; *Macromolecules 2003*, 36, 1522-1525.
Chen, Yu et al.: "Synthesis of Multihydroxyl Branched Polyethers by Cationic Copolymerization of 3,3-Bis(hydroxymethyl)oxetane and 3-Ethyl-3-(hydroxymethyl)oxetane"; *Journal of Polymer Science*: Part A: Polymer Chemistry, vol. 40, 1991-2002; 2002 Wiley Periodicals, Inc.
Nishimura, Tomonari et al.: "Chemoselective isomerization of amide-substituted oxetanes with Lewis acid to give oxazine derivatives or bicyclic amide acetals"; *Chem. Commun.*, 1998; pp. 43-44.
Miwa, Yoshiyuki et al.: "Polymerization of Bis-Oxetanes Consisting of Oligo-Ethylene Oxide Chain with Lithium Salts as Initiators"; *Polym. J.*, vol. 33, No. 8, 2001; pp. 568-574.
Ichikawa, Eiko et al.: "Synthesis of Oxetanocin A and Related Unusual Nucleosides with Bis(hydroxymethyl)-branched Sugars"; *Synthesis 2002*, No. 1, 28 12 2001; Georg Thieme Verlag Stuttgart, NY; pp. 1-28.
Minegishi, Shouji et al.: "Synthesis of Polyphosphonates Containing Pendant Chloromethyl Groups by the Polyaddition of Bis(oxetanes)s with Phosphonic Dichlorides"; *Journal of Polymer Science*: Part A: Polymer Chemistry, vol. 40 3835-3846; 2002 Wiley Periodicals, Inc.
Rosenbaum, Dr. Barry et al.: "Develop Better Coatings"; *OMNOVA Solutions Inc.*, Akron, OH; pp. 1-5.
Sasaki, Hiroshi: "Application of Oxetane Monomers for UV-Curable Materials"; RadTech 2002; Tech. Conf. Proceedings; pp. 64-78.
Carter, Wells et al.: "New Oxetane Derivative Reactive Filuent For Cationic UV Cure"; *RadTech 2000*; Tech. Proceed.; pp. 641-649.
Crivello, J. V. et al.: "Diaryliodonium Salts as Thermal Initiators of Cationic Polymerization"; *Journal of Polymer Science*: Polymer Chemistry Ed, vol. 21, 97-109 (1983); John Wiley & Sons, Inc.
Lu, Yong-Hong et al.: "Synthesis of Side-Chain Liquid Crystalline Polyoxetanes Containing 4-(Alkanyloxy)phenyl *trans*-4-Alkylcyclohexanoate Side Groups"; *1995 American Chem. Society*; pp. 1673-1680.
Hsu, Li-Ling et al.: "Studies on the Synthesis and Properties of Ferroelectric Side Chain Liquid Crystalline Polyoxetanes"; *Journal of Polymer Science*: Part A: Polymer Chemistry; vol. 35, 2843-2855; (1997); John Wiley & Sons, Inc.
Kawakami, Yusuke et al.: "Synthesis and Thermal Transition of Side-chain Liquid Crystalline Polyoxetanes Having Laterally Attached Mesogenic Group"; *Polymer International*; 0959-8103/93; Great Britain.

(Continued)

Primary Examiner—Kamal A. Saeed
(74) Attorney, Agent, or Firm—Jane E. Gennaro

(57) ABSTRACT

Polymeric compounds containing an oxetane functionality and a maleimide functionality have the structure

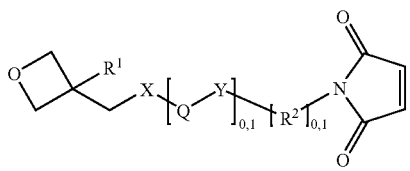

in which polymer is a polymeric backbone, m and n are integers from 2 to 500, $R^1$ is methyl or ethyl, $R^2$ is a divalent hydrocarbon, and W and Z are independently an ether, carboxyl, ester, carbamate, urea or amide linking functionality.

1 Claim, No Drawings

OTHER PUBLICATIONS

Kawakami, Yusuke et al.: "Synthesis of Liquid Crystalline Polymers with a Polyoxetane Main Chain"; *Macromolecules*; vol. 24, No. 16, 1991; pp. 4531-4537.

Kawakami, Yusuke et al.: "Smectic liquid crystalline polyoxetane with novel mesogenic group"; *Polymer Bulletin 25*; Springer-Verlag 1991; pp. 439-442.

Crivello, J.V. et al.: "Photoinitiated Cationic Polymerization With Multifunctional Vinyl Ether Monomers"; *Journal of Radiation Curing*, Jan. 1983; pp. 6-13.

Ishizone, Takashi et al.: "Protection and Polymerization of Functional Monomers. 29. Syntheses of Well-Defined Poly[(4-vinylphenyl)acetic acid], Poly[3-(4-vinylphenyl)propionic acid], and Poly(3-vinylbenzoic acid) by Means of Anionic Living Polymerizations of Protected Monomers Bearing Bicyclic Ortho Ester Moieties"; *Macromolecules 1999*, 32, 1453-1462.

Sato, Kazuya et al.: "New Reactive Polymer Carrying a Pendant Oxetane Ring"; *Macromolecules 1992*, 25, 1198-1199; Communications to the Editor.

Moussa, K. et al.: "Light-Induced Polymerization of New Highly Reactive Acrylic Monomers"; *Journal of Polymer Science*: Part A: Polymer Chemistry, vol. 31, 2197-2203 (1993); John Wiley & Sons, Inc.

Kawakami, Yusuke et al.: "Synthesis of Liquid Crystalline Polyoxetanes Bearing Cyanobiphenyl Mesogen and Siloxane-Containing Substituent in the Repeating Unit"; *Polymer Journal*, vol. 28, No. 10, pp. 845-850 (1996).

Crivello, J. V. et al.: "Synthesis and Photopolymerization of Silicon-Containing Multifunctional Oxetane Monomers"; *J.M.S.-Pure Appl. Chem.*, A30(2 & 3), pp. 173-187 (1993); Marcel Dekker, Inc.

Chappelow, C. C. et al.: "Photoreactivity of Vinyl Ether/Oxirane-Based Resin Systems"; *Journal of Applied Polymer Science*, vol. 86, 314-326 (2002); Wiley Periodicals, Inc.

Toagosei Co. Ltd.: "Developing Monomers".

"Oxetane"; Copyright 2000 American Chemical Society.

Hou, Jian et al.: "Synthesis of a Star-Shaped Copolymer with a Hyperbranched Poly(3-methyl-3-oxetanemethanol) Core and Tetrahydrofuran Arms by One-Pot Copolymerization"; *Macromol. Rapid Commun.* 2002, 23, 456-459.

Xu, Jun et al.: "Study On Cationic Ring-Opening Polymerization Mechanism of 3-Ethyl-3-Hydroxymethyl Oxetane"; *J. Macromol. Sci.*- Pure Appl. Chem., A39(5), 431-445 (2002); Marcel Dekker, Inc.

Suzuki, Hiroshi et al.: "Photo-cationic curable materials using cationic polymerizable monomers such as epoxides and vinyl ether derivatives"; *Polymer Preprints 2001*, 42(2), 733.

Kanoh, Shigeyoshi et al.: "Monomer-Isomerization Polymerization of 3-Methyl-3-(phthalimidomethyl)oxetane with Two Different Ring-Opening Courses"; *Macromolecules 1999*, 32, 2438-2448; 1999 American Chemical Society.

Jansen, Johan F.G.A. et al.: "Effect of Dipole Moment on the Maximum Rate of Photoinitiated Acrylate Polymerizations"; *Macromolecules 2002*, 35, 7529-7531; 2002 American Chemical Society; Communications to the Editor.

Crivello, J. V. et al.: "Structure And Reactivity Relationships In The Photoinitiated Cationic Polymerization Of Oxetane Monomers"; *J.M.S.-Pure Appl. Chem.*, A30(2&3), pp. 189-206 (1993); Marcel Dekker, Inc.

Machida, Shigeru et al.: "The Highly *Syn*-Selective Michael Reaction Of Enamines With 2-(1-Alkenyl)-1,3-Dioxolan-2-Ylium Cations Generated From 2,2-Dimethoxyethyl 2-Alkenoates In Situ"; *Tetrahedron* vol. 47, No. 23, pp. 3737-3752, 1991; 1991 Pergamon Press plc.

Motoi, Masatoshi et al.: "Preparation of Polyoxetane-Polystyrene Composite Resins and Their Use as Polymeric Supports of Phase-Transfer Catalysts"; *Polymer Journal*, vol. 21, No. 12, pp. 987-1001 (1989).

Pattison, Dexter B.: "Cyclic Ethers Made by Pyrolysis of Carbonate Esters"; *Orchem Laboratories* E.I. DuPont; Jan. 17, 1957.

Smith, Tara J. et al.: "Ring Opening of 2-Ethyl-2-Hydroxymethyl Oxetane Under Basic Conditions"; *Polymer Preprints 2002*, 43(2), 984.

Nishikubo, Tadatomi et al.: "Synthesis of Alternating Copolyesters of Oxetanes With Cyclic Carboxylic Anhydrides Using Quaternary Onium Salts"; *Polymer Preprints 2002*, 43(2), 1135-1136.

Amass, A. J. et al.: "Studies In Ring-Opening Polymerization-XII. The Ring-Opening Polymerization Of Oxetane To Living Polymers Using A Porphinato-Aluminum Catalyst"; *Eur. Polym. J.* vol. 30, No. 5, pp. 641-646, 1994, Elsevier Science Ltd. 1994.

Takeuchi, Daisuke et al.: "Controlled Coordinate Anionic Polymerization of Oxetane by Novel Initiating Systems: Onium Salts/Bulky Organoaluminum Diphenolates"; *Macromolecules 1996*, 29, 8096-8100.

Kanoh, Shigeyoshi et al.: "Cationic Monomer-Isomerization Polymerization of Oxetanes Having an Ester Substituent, to Give Poly(orthoester) or Polyether"; *Macromol. Chem. Phys.* 2002, 203, 511-521; Wiley-Vch.

Kanoh, Shigeyoshi et al.: "Double Isomerization of Oxetane Amides to Azetidine Esters with Ring Expansion and Contraction"; *J. Org. Chem.* 2000, 65, 2253-2256, 2000 American Chemical Society.

Kudo, Hiroto et al.: "Synthesis of a Hetero Telechelic Hyperbranched Polyether. Anionic Ring-Opening Polymerization of 3-Ethyl-3-(hydroxymethyl)oxetane Using Potassium *tert*-Butoxide as an Initiator"; Short Communications; *Polym. J.*, vol. 35, No. 1, 2003; pp. 88-91.

Ueyama, Akihiko et al.: "Preparation of Polyoxetane Resins Having Polyoxirane Segments in the Pendant and Cross-Linking Chains and Uses as Polymeric Solvents for Alkali-Metal Ions"; *Polymer Journal*, vol. 34, No. 12, pp. 944-953 (2002).

Singha, Nikhil K. et al.: "Atom Transfer Radical Copolymerization (ATRCP) Of A Monomer Bearing An Oxetane Group"; *Polymer Preprints 2002*, 43(2), 165.

Sasaki, H. et al.: "The Synthesis, Characterization, And Photoinitiated Cationic Polymerization Of Difunctional Oxetanes"; *J.M.S.-Pure Appl. Chem.*, A29(10), pp. 915-930 (1992).

Hsieh, H.L.: "Terpolymerization of Cyclic Ethers with Cyclic Anhydride"; J. Macromol. Sci.-Chem., A7(7), pp. 1525-1535 (1973).

Bach, Thorsten: "The Paterno-Buchi Reaction of 3-Heteroatom-Substituted Alkenes as a Stereoselective Entry to Polyfunctional Cyclic and Acyclic Molecules"; Liebigs. Ann/Recueil 1997, 1627-1634.

Bach, Thorsten: "Synthesis of syn-and anti-1,2-Amino Alcohols by Regioselective Ring Opening Reactions of cis-3-Aminooxetanes"; Tetrahedron Letters, vol. 38, No. 21, pp. 3707-3710, 1997.

Meijer, Von E.W. et al: "Chiralitat nur im angeregten Zustand"; Angew Chem., 100 (1988) Nr. 7.

* cited by examiner

POLYMER COMPOUNDS CONTAINING OXETANE AND MALEIMIDE FUNCTIONALITY

This Application is a divisional of U.S. patent application Ser. No. 10/430,085, filed May 06, 2003, now issued as U.S. Pat. No. 6,982,338.

FIELD OF THE INVENTION

This invention relates to oxetane compounds containing maleimide functionality.

BACKGROUND OF THE INVENTION

Oxetanes are highly reactive cyclic ethers that can undergo both cationic and anionic ring opening homopolymerization. Maleimide compounds are capable of free radical polymerization.

SUMMARY OF THE INVENTION

This invention relates to compounds that contain an oxetane functionality and a maleimide functionality. These compounds can be homopolymerizable in reactions in which the oxetane can undergo cationic or anionic ring opening, or polymerizable with compounds such as electron donor compounds. The dual functionality allows for dual cure processing, both thermal cure or radiation cure. This capability makes them attractive for use in many applications, such as, adhesives, coatings, encapsulants, and composites.

DETAILED DESCRIPTION OF THE INVENTION

In one embodiment, the compounds of this invention can represented by the formula

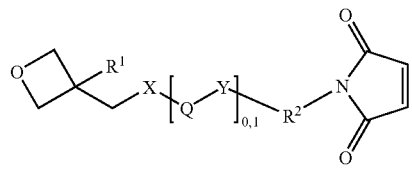

in which $R^1$ is a methyl or ethyl group; $R^2$ is a divalent hydrocarbon; X and Y independently are a direct bond, or an ether, ester, amide, or carbamate group; and Q is a divalent hydrocarbon.

The starting maleimide compound may be small molecule, for example, 6-maleimidocaproic acid, 3-maleimidopropionic acid, N-(6-hydroxyhexyl) maleimide, N-(3-hydroxypropyl)maleimide, and N-(5-isocyanatopentyl)maleimide, or may be an oligomeric or polymeric material containing prepared by reacting, for example, 6-maleimidocaproic acid or 3-maleimidopropionic acid with one functionality on a difunctional oligomer or polymer.

Whether the starting maleimide compound is a small molecule or an oligomeric or polymeric material, it will contain a maleimide functionality represented by the structural formula

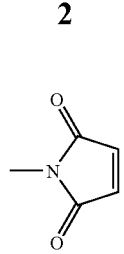

and a second functionality reactive with a second functionality on the starting oxetane compound. For example, the maleimide starting materials disclosed above contain carboxyl, hydroxyl, or isocyanato functionality in addition to the maleimide functionality.

The starting oxetane compound may be a small molecule or an oligomeric or polymeric molecule, prepared, for example, by reacting one of the small molecule oxetane starting compounds disclosed below with one functionality on a difunctional oligomer or polymer. In either case, it will contain an oxetane functionality represented by the structure

and a second functionality reactive with the second functionality on the maleimide starting compound.

Suitable starting oxetane compounds that are small molecules include, for example, (a) alcohols, such as, 3-methyl-3-hydroxymethyloxetane, 3-ethyl-3-hydroxymethyloxetane;

 

(b) halides, such as, 3-methyl-3-bromomethyloxetane, 3-ethyl-3-bromomethyloxetane, which can be prepared by the reaction of an alcohol from (a) with $CBr_4$ as is known in the art;

 

(c) alkyl halides, such as, 3-methyl-3-alkylbromomethyloxetane, 3-ethyl-3-alkylbromomethyloxetane, which can be prepared from the reaction of an alkyl dibromide compound with an oxetane alcohol from (a) as is known in the art;

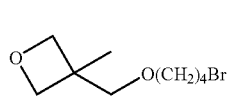 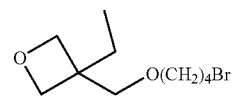

and (d) tosylates, such as, 3-methyl-3-tosylmethyloxetane, 3-ethyl-3-tosylmethyl-oxetane, which can be prepared from p-toluenesulfonyl chloride:

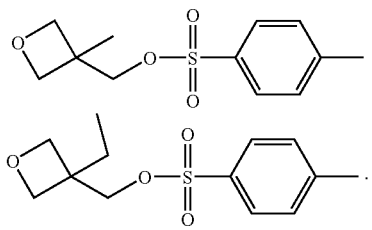

When a longer chain and higher molecular weight compound containing maleimide and oxetane is desired, either the starting maleimide compound or the starting oxetane compound, or both, may be extended by reaction with a difunctional oligomeric or polymeric material. The second functionality on this oligomeric or polymeric material must be reactive with the oxetane starting compound if the first reaction was between the maleimide starting compound and the difunctional oligomeric or polymeric material, and with the maleimide starting compound if the first reaction was between the oxetane starting compound and the difunctional oligomeric or polymeric material. Examples of suitable and commercially available oligomers and polymers include dimer diol and poly(butadiene) with terminal hydroxyl functionality.

In the case in which both the oxetane and maleimide compounds are extended by reaction with a difunctional oligomer or polymer, Q may also contain a functionality, for example, an ether, ester, carbamate, or urea functionality, resulting from the reaction of the two oligomeric or polymeric starting materials.

In general, the inventive compounds containing oxetane and maleimide functionality are prepared by reacting together a starting compound containing oxetane functionality and a second functionality and a starting compound containing maleimide functionality and a second functionality reactive with the second functionality on the oxetane compound. Typical reaction schemes include well known addition, substitution, and condensation reactions.

In a further embodiment, the compounds of this invention include polymeric compounds that contain more than one oxetane and more than one maleimide functionality. Such compounds are prepared from a polymeric starting compound from which depend functionalities that are reactive with the starting oxetane compound and the starting maleimide compound.

The polymeric compound will have the structure

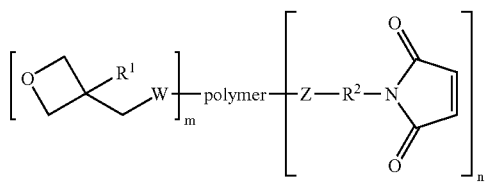

in which polymer is a polymeric backbone from which depend the oxetane and maleimide functionalities, m and n are integers that will vary with the level of oxetane and maleimide functionality added by the practitioner and typically will be from 2 to 500, $R^1$ is methyl or ethyl, $R^2$ is a divalent hydrocarbon, and W and Z are independently a linking functionality, such as, an ether, carboxyl, ester, carbamate, or urea, which is created through the reaction of a pendant functionality on the polymer and a corresponding reactive functionality on the starting oxetane compound or starting maleimide compound.

The pendant functionalities on the polymer may be connected to the polymeric backbone by a hydrocarbon, for example, one having one to twenty carbons, that itself is dependent from the polymeric backbone. For purposes of this specification, those dependent moieties will be deemed to be part of the polymeric backbone.

An example of a commercially available and suitable polymeric backbone is poly(butadiene) having pendant hydroxyl groups. The pendant hydroxyl groups can be reacted with the oxetane starting compound containing the tosyl leaving group and with 6-maleimidocaproic acid. In this case, the linking group W will be an ether functionality and Z will contain an ester functionality.

As a further example, a poly(butadiene) having pendant carboxylic acid functionality can react with the hydroxyl functionality on either of the hydroxyl oxetane starting materials and with the hydroxyl functionality on N-(6-hydroxyhexyl) maleimide, N-(3-hydroxypropyl) maleimide. In this case, the W and Z groups will be an ester functionality. In the case where N-(5-isocyanatopentyl) maleimide is reacted with a pendant hydroxyl group, the Z group will be an amide functionality.

Polymeric starting material can be purchased commercially, for example, there are available acrylonitrile-butadiene rubbers from Zeon Chemicals and styrene-acrylic copolymers from Johnson Polymer. The pendant functionalities from these polymers are hydroxyl or carboxylic acid functionality.

Other starting polymeric materials can be synthesized from acrylic and/or vinyl monomers using standard polymerization techniques known to those skilled in the art. Suitable acrylic monomers include $\alpha,\beta$-unsaturated mono and dicarboxylic acids having three to five carbon atoms and acrylate ester monomers (alkyl esters of acrylic and methacrylic acid in which the alkyl groups contain one to fourteen carbon atoms).

Examples are methyl acryate, methyl methacrylate, n-octyl acrylate, n-nonyl methacrylate, and their corresponding branched isomers, such as, 2-ethylhexyl acrylate. Suitable vinyl monomers include vinyl esters, vinyl ethers, vinyl halides, vinylidene halides, and nitriles of ethylenically unsaturated hydrocarbons. Examples are vinyl acetate, acrylamide, 1-octyl acrylamide, acrylic acid, vinyl ethyl ether, vinyl chloride, vinylidene chloride, acrylonitrile, maleic anhydride, and styrene.

Other polymeric starting materials can be prepared from conjugated diene and/or vinyl monomers using standard polymerization techniques known to those skilled in the art. Suitable conjugated diene monomers include butadiene-1, 3,2-chlorobutadiene-1,3, isoprene, piperylene and conjugated hexadienes. Suitable vinyl monomers include styrene, $\alpha$-methylstyrene, divinylbenzene, vinyl chloride, vinyl acetate, vinylidene chloride, methyl methacrylate, ethyl acrylate, vinylpyridine, acrylonitrile, methacrylonitrile, methacrylic acid, itaconic acid and acrylic acid.

Those skilled in the art have sufficient expertise to choose the appropriate combination of those monomers and subsequent reactions to be able to add pendant functionality, for example, hydroxyl and carboxyl functionality, for adding the oxetane and maleimide functionalities as disclosed in this specification.

EXAMPLES

Example 1

Preparation of Ethyl Oxetane Maleimide

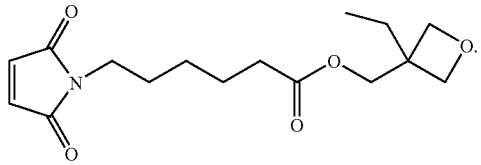

250-ml 4-neck round bottom flask was equipped with a mechanical stirrer, thermometer, nitrogen purge and slow-addition funnel. 6-Maleimideocaproic acid (MCA) (25.59 g, 0.1213 mole), 3-ethyl-3-oxetane methanol (14.10 g, 0.1213 mole), 4-dimethylaminopyridine (1.5 g, 0.0121 mole) and toluene (60 ml) were charged to the flask resulting in a dark gold solution with a minor amount of undissolved solids. The flask contents were chilled to 0-5° C. with mixing. A solution prepared from 1,3-dicyclohexyl-carbodiimide (DCC, 25.00 g, 0.1213 mole) and toluene (20 ml) was then charged to the slow-addition funnel. The DCC/toluene solution was added to the flask over 30 minutes while maintaining a reaction temperature between 10 and 15° C.

Stirring was continued for six hours at 10-15° C. after which time thin layer chromatography (1/1 ethyl acetate/hexane) indicated that both the oxetane and DCC were consumed. The reaction was stopped and white solids were filtered from the red-orange solution. Next, this reaction solution was washed three times with an equivalent volume of a saturated sodium bicarbonate solution. Toluene was then stripped from the reaction in vacuo and replaced with a solution of ethyl acetate and hexane (1/1 by volume). A chromatography column was then utilized to isolate a qualitative amount of a clear yellow oil with a viscosity of 270 cPs. The compound had a weight loss of 15% at 200° C. as measured by TGA.

$H^1$-NMR: δ6.55 (s, 2H), 4.55 (d, 2H), 4.45 (d, 2H), 4.21 (s, 2H), 3.41 -3.52 (t, 2H), 2.25 -2.42 (t, 2H), 1.51-1.79 (m, 4H), 1.11-1.41 (m, 4H), 0.83-0.95 (t, 3H).

Example 2

Preparation of Methyl Oxetane Maleimide

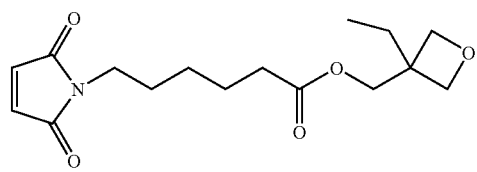

The starting compound for methyl oxetane maleimide is maleimidocaproic chloride having the structure

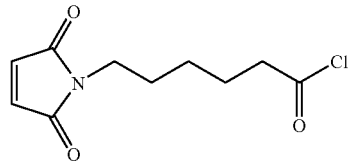

and prepared as follows: A 500-ml 4-neck round bottom flask was equipped with a condenser, mechanical mixer, thermometer, and hot oil bath and then charged with maleimidocaproic acid (MCA) (40.00 g, 0.1896 mole), dimethylformamide (3 drops) and toluene (125 ml). The flask contents were heated to 85° C. and mixed until all solids were dissolved. Subsequently, the hot solution was decanted into a similar flask fitted with a mechanical mixer, bubbler, slow-addition funnel and ice bath. The reaction solution was then chilled with mixing.

Oxalyl chloride (36.09 g 0.2844 mole) was added to the reaction flask via slow-addition funnel while maintaining a reaction temperature of 5-10° C. Following the oxalyl chloride addition, the ice bath was removed and the reaction was allowed to warm to room temperature. As the reaction temperature increased, the bubbler indicated that gas was being generated. The reaction was left to mix over night resulting in a very dark solution. It was then decanted into a 1L single-neck round bottom flask and stripped of toluene under vacuum. Toluene (200 ml) was then added to the flask and stripped three times to reduce acidity. The product was maleimidocaproic chloride.

3-Methyl-3-oxetane methanol (19.36 g, 0.1896 mole), triethylamine (19.19 g, 0.1896 mole), 4-dimethylaminopyridine (2.32 g, 0.0190 mole) and dichloromethane (175 ml) were combined in a 500-ml 4-neck round bottom flask equipped with a magnetic stir bar, slow-addition funnel, drying tube and ice bath. A nitrogen purge was used to displace humid air within the flask. The reaction solution was then chilled with mixing to 10° C. and a solution of maleimideocaproic chloride (43.4 g, 0.1896 mole) in 25 ml dichloromethane was added at a rate slow enough to maintain this temperature.

Following the addition, the resulting dark brown solution was mixed at room temperature over-night. Thin-layer chromatography (1/1 vol., ethyl acetate/hexane) indicated that the reaction was complete based on the depletion of maleimidocaproic chloride. White solids were filtered from the reaction solution which was then washed four times with distilled water (300 ml each). Methylene chloride was stripped from the reaction solution via roto-evaporation and replaced with an ethyl acetate/hexane solution (2/1, respectively, by volume). The dark brown solution was then passed through a column of silica gel to purify. Next, the solvent was stripped in vacuo resulting in a clear orange product with a viscosity of 750 cPs. The compound had a weight loss of 8% at 200° C. as measured by TGA.

H$^1$-NMR: δ6.65 (s, 2H), 4.45 (d, 2H), 4.31 (d, 2H), 4.06 (s, 2H), 3.46-3.61 (m, 2H), 2.31 (t, 2H), 1.45-1.65 (m, 4H), 1.16-1.29 (m, 5H).
What is claimed:
1. An oxetane and maleimide compound of Formula 5
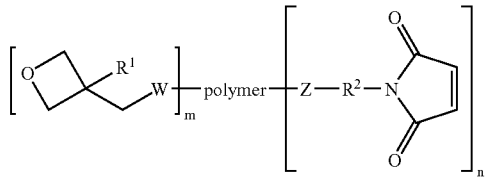
in which
polymer is a polymeric backbone
m and n are integers from 2 to 500
R$^1$ is methyl or ethyl
R$^2$ is a divalent hydrocarbon
W and Z are independently an ether, carboxyl, ester, carbamate, urea or amide linking functionality.
* * * * *